US006248589B1

(12) United States Patent
Hagedorn et al.

(10) Patent No.: US 6,248,589 B1
(45) Date of Patent: Jun. 19, 2001

(54) RECOMBINANT HEPATITIS C VIRUS RNA REPLICASE

(75) Inventors: Curt H. Hagedorn, Atlanta, GA (US); Reinoldus H. Al, Mysen (NO)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/337,028

(22) Filed: Jun. 25, 1999

Related U.S. Application Data

(62) Division of application No. 08/722,806, filed on Sep. 27, 1996, now Pat. No. 5,981,247.
(60) Provisional application No. 60/004,382, filed on Sep. 27, 1995.

(51) Int. Cl.[7] .................................................. C12N 15/10

(52) U.S. Cl. ........................................... 435/471; 435/194
(58) Field of Search ..................................... 435/471, 194

(56) References Cited

U.S. PATENT DOCUMENTS 5,350,671 9/1994 Houghton et al. ....................... 435/5

OTHER PUBLICATIONS

Bartenschlager, R. et al. "Kinetic and Structural Analyses of Hepatitis C. Virus Polyprotein Processing"; (1994) *Journal of Virology* 68(8):5045–5055.*
Lin, C. et al. "Hepatitis C Virus NS3 Serine Proteinase; *trans*–Cleavage Requirements and Processing Kinetics"; (1994) *Journal of Virology* 68(12):8147–8157.*
Behrens, S–E. et al. "Identification and properties of the RNA–dependent RNA polymerase of hepatitis C virus"; (1996) *The EMBO Journal* 15:12–22.
Sankar, S. et al. "Expression, Purification, and Recombinanat Encephalomyocarditis Virus RNA–Dependent RNA Polymerase"; (1991) *Journal of Virology* 65:2993–3000.
Rothstein, M.A. et al. "Enzymatic Activity of Poliovirus RNA Polymerase Synthesized in *Escherichia coli* from Viral cDNA"; (1988) Virology 164–301–308.
Hirowatari, Y. et al. "Expression and processing of putative nonstructural proteins of hepatitis C virus in insect cell using baculovirus vector"; (1995) *Virus Research* 35:43–61.
Kuo, G. et a. "An Assay for Circulating Antibodies to a Major Etilogic Virus of Human Non–A, Non–B Hepatitis"; (1989) *Science* 244:362–364.
Choo, Q.–L. et a. "Genetic Organization and Diversity of the Hepatitis C Virus"; (1991) *Proc. Natl. Acad. Sci. USA* 88:2451–2455.
Lin, C. et al. Processing in the Hepatitis C Virus E2–NS2 Region: Identification of p7 and Two Distinct E2–Specific Products with Different C Termini; (1994) *Journal of Virology*68:5063–5073.
Grakoui, A. et al. "Expression and Identification of Hepatitis C Virus Polyprotein Cleavage Products" (1993) *Journal of Virology* 67:1385–1395.

Koonin, E.V. "The Phylogeny of RNA–dependent RNA polymerase of positive–strand RNA viruses"; (1991) *Journal of General Virology* 72:2197–2206.

Wu, J. et al. Identifying Substrate Motifs of Protein Kinases by a Random Library Approach; (1994) *Biochemistry* 33: 14825–14833.

Ohlmeyer, Michael H.J. et al. "Complex Synthetic ChemicalLibraries indexed with Molecular Tags"; (1993) *Proc. Natl. Acad. Sci. USA* 90:10922–10926.

Tanaka, T. et al. "A Novel Sequence Found at the 3'Terminus of Hepatitis C Virus Genome"; (1995) *Biochem. Biophys. Res. Commun.* 215:74–749.

Al, R.H. et al. "Characterization of Active Hepatitis C Virus RNA–Dependent RNA Polymerase Expressed in *E. coli*"; Abstract presented at Cold Spring Harbor Meetting on Molecular Approaches to the Control of Infectious Diseases, held Sept. 9–13, 1996.

Hagedorn, C.H. et al. "Expression in *E. coli* and Characterization of the Hepatitis C Virus NS5B gene Product"; Abstract of Poster presentation at IRBM Workshop on Molecular Mechanism of RNA Replication, held May 24–28, 1996, Alghero, Sardinia, Italy.

Al. R.H. et al. "Purfiation and Characterization of Recombinant Enzymatically Active, Hepatitis C Rna Polymerase (HCV rRDRP)"; Abstract of presentation at annual Meetings of American Gastroenterological Association and American Association for the Study if Liver Diseases, held May 19–22, 1996.

Al, R.H. et al. "Expression and Characterization of the NS5B (RNA–Dependent RNA Polymerase) Gene of Hepatitis C Virus"; Abstract of presentation at Meeting of American Association for the Study of Liver Diseases, held Nov. 3–7, 1995.

* cited by examiner

*Primary Examiner*—Charles L. Patterson, Jr.
(74) *Attorney, Agent, or Firm*—Greenlee Winner and Sullivan, PC

(57) ABSTRACT

A recombinant RNA-dependent RNA polymerase of hepatitis C virus (r-HCV-RDRP) coding DNA was cloned and expressed yielding active enzyme in vitro. The r-HCV-RDRP can include up to 20 added amino acids and up to nine deleted or substituted amino acids at the $NH_2$-terminus of the encoded amino acid sequence. The invention provides method to solubilize r-HCV-RDRP from a host cell lysate and purified r-HCV-RDRP. Methods for screening for inhibitors of r-HCV-RDRP in vitro, for making stably transfected mammalian cells expressing r-HCV-RDRP and for in vivo testing of r-HCV-RDRP inhibitors in vivo are disclosed. The invention provides antibodies to r-HCV-RDRP and methods for detecting antibodies to HCV-RDRP in serum of human patients.

5 Claims, 7 Drawing Sheets

RECOMBINANT HEPATITIS C VIRUS RNA REPLICASE

Figure 1:
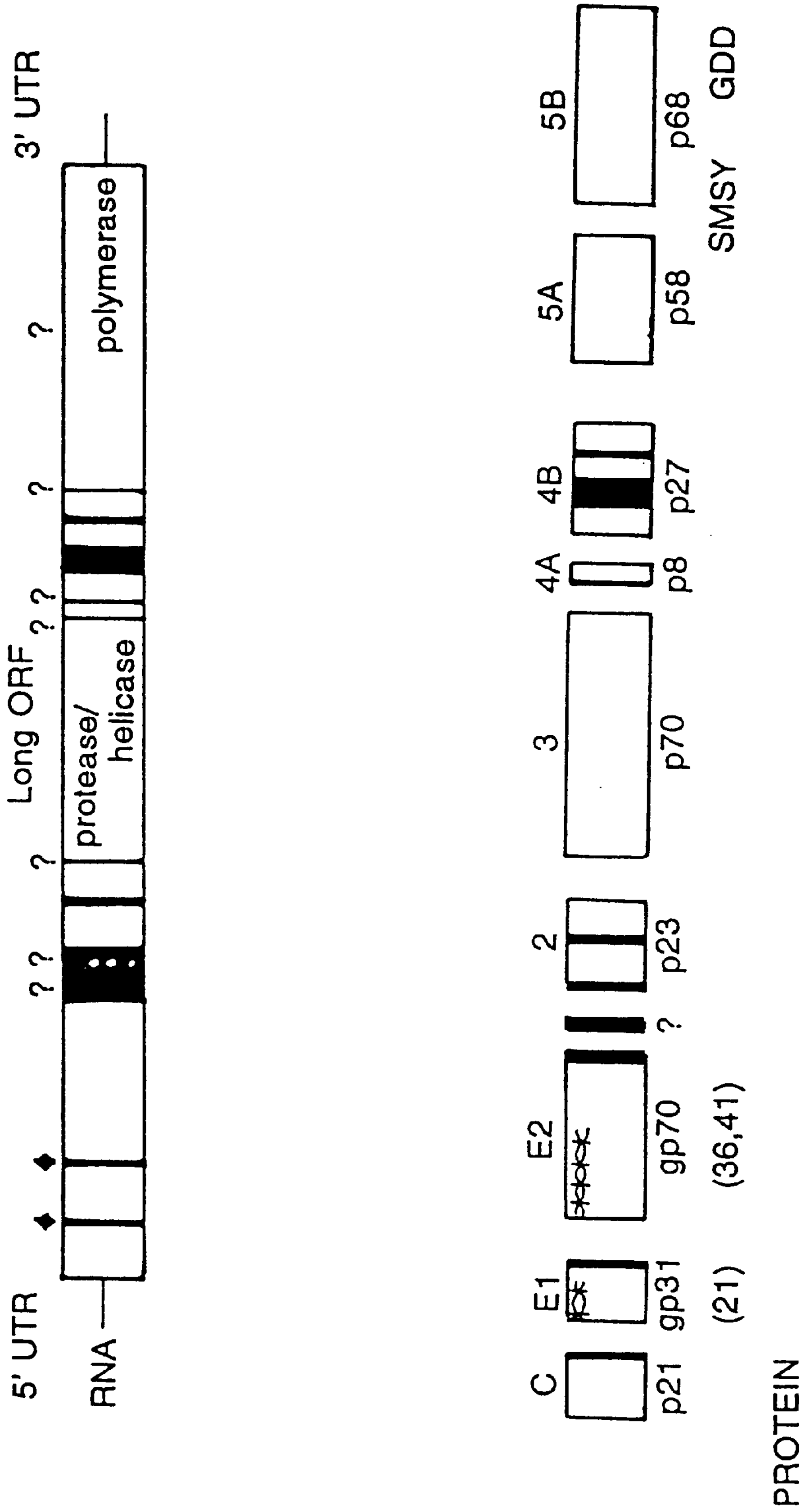

This application claims priority from U.S. Provisional Application Ser. No. 60/004,383, filed Sep. 27, 1995 and is a division of U.S. patent application Ser. No. 08/722,806 filed Sep. 27, 1996 now U.S. Pat. No. 5,981,247.

FIELD OF THE INVENTION

The present invention relates Hepatitis-C virus (HCV), specifically to expression and purification of an RNA-dependent RNA polymerase (RDRP) encoded by the HCV genome, to antibodies directed against HCV-RDRP and to methods of using the enzyme to diagnose chronic HCV infections and to screen for antiviral agents effective against HCV.

BACKGROUND OF THE INVENTION

HCV is the major causative agent for post-transfusion and for sporadic non A, non B hepatitis (Alter, H. J. (1990) *J. Gastro. Hepatol.* 1:78–94; Dienstag, J. L. (1983) *Gastro* 85:439–462). Despite improved screening, HCV still accounts for at least 25% of the acute viral hepatitis in many countries (Alter, H. J. (1990) supra; Dienstag, J. L. (1983) supra; Alter, M. J. et al. (1990a) *J.A.M.A.* 264:2231–2235; Alter, M. J. et al (1992) *N. Engl. J. Med.* 327:1899–1905; Alter, M. J. et al .(1990b) *N. Engl. J. Med.* 321:1494–1500). Infection by HCV is insidious in a high proportion of chronically infected (and infectious) carriers who may not experience clinical symptoms for many years. The high rate of progression of acute infection to chronic infection (70–100%) and liver disease (>50%), its world-wide distribution and lack of a vaccine make HCV a significant cause of morbidity and mortality.

HCV is an enveloped virus whose genome is a 9.4 kb single-stranded RNA (sense(+)) encoding a single polyprotein that is processed by proteolysis to yield at least 9 proteins. HCV is related to pestiviruses and flaviviruses (Choo, Q-L. et al. (1989) Science 244:362–364; Choo, Q-L. et al. (1991) *Proc. Natl. Acad. Sci. USA* 88:2451–2455. Reinfection of previously HCV-infected chimpanzees suggests that protective immunity is transient or non-existent (Farci, P. et al (1992) Science 258:135–140). Furthermore, results of recent vaccine trials suggest that development of an effective vaccine is remote (Houghton, M. et al. (1994) *2nd Internat. Meeting on Hepatitis C* (San Diego)). Attempted treatment of chronic HCV infection using existing antiviral agents produces low cure rates and serious side effects. (Dienstag, J. L. (1983) supra.)

The nucleotide sequence of the HCV genome has been cloned and a single open reading frame has been identified. Using a vaccinia virus expression system, several cleavage products have been tentatively identified. (Lin, C. et al. (1994) *J. Virol.* 68:5063–5073; Grakoui, A. et al. (1993) *J. Virol.* 67:1385–1395.) The various putative cleavage products were recognized by antibodies raised against various peptides synthesized from amino acid sequences deduced from various segments of the coding regions. Sizes of antibody-reactive peptides were estimated by SDS-PAGE (See FIG. 1). The non-structural protein designated 5B (NS5B) has been shown to have an amino-terminal sequence SMSY (Ser-Met-Ser-Tyr). The NS5B region encodes a 68 kd protein (p68) which contains an internal GDD (Gly-Asp-Asp) motif found in RNA-dependent RNA polymerases of other RNA viruses (Koonin, E. V. (1991) *J. Gen. Virol.* 72:2197–2206). However, no polymerase activity has been detected for HCV p68. In fact, the question has been raised that the 5B protein (p68) alone does not encode an active RNA-dependent RNA polymerase enzyme and that another subunit, possibly the NS5A gene product, is essential to catalytic activity. Prior attempts by the inventors and others to express the NS5B coding region as a fusion protein, using existing expression systems that facilitate purification of the fusion product, and specific cleavage have failed to yield any active polymerase.

SUMMARY OF THE INVENTION

The present invention provides a recombinant protein of HCV having RDRP activity (r-HCV-RDRP) obtainable by expression in a host mammalian or bacterial cell of a modified NS5B coding region of HCV. The modification includes addition at the amino terminus of a methionine residue and optionally from 1–20 additional amino acids interposed between the N-terminal methionine and the N-terminal serine of unmodified NS5B gene product. The modification also includes deletion at the amino terminus of up to 9 amino acids to provide an amino-terminal methionine. Two methionines occur naturally according to the deduced sequence of wild-type HCV-RDRP. Therefore, modification includes deletion to remove amino acids lying N-terminal to either methionine or, alternatively, deletion to some intermediate point between the two methionines plus addition of an N-terminal methionine codon. A combination of deletions and insertions, within the limits described is also contemplated. Added amino acid sequence can be devised to create a specific protease cleavage site to permit post translational modification of the recombinant HCV-RDRP expression produce, in vivo or in vitro. Such post-transcriptional modification can be used to generate exactly the amino acid sequence encoded by NS5B, having an N-terminal serine. Added amino acid sequence can be devised to generate an affinity ligand binding site, for convenience and ease of purification. The data reported herein were obtained with a r-HCV-RDRP having an N-terminal MA (Met-Ala) dipeptide, giving an N-terminal sequence MASMSY (SEQ ID NO:6) instead of the predicted SMSY sequence of the wild-type processed protein. The coding sequence of NS5B is accordingly modified to include a met codon (ATG) at the 5'-end, as well as, optionally, codons for other amino acids to be included or deleted. Minimal modifications are preferred, in order to avoid potential deleterious effects on enzyme activity, and to avoid creating artificial epitopes. The r-HCV-RDRP can be expressed in *E. coli* and in mammalian cells to yield active RDRP. The expression of active r-HCV-RDRP in *E. coli* demonstrates that no other HCV-encoded protein is necessary for polymerase activity.

The invention further provides r-HCV-RDRP in solubilized form, and a method of solubilization without destroying activity.

The invention also provides methods for purifying solubilized HCV-RDRP. One such method, to be used in combination with others, is affinity chromatography, using antibody to r-HCV-RDRP as the affinity ligand. Other affinity ligands are obtained by a combinatorial library approach as described, e.g., by Wu, J. et al. (1994) *Biochemistry* 33:14825–14833; and Ohlmeyer, M. H. J. et al. (1993) *Procl. Nat. Acad. Sci. USA* 90:10922–10926.

In addition, the invention provides polyclonal or monoclonal antibodies specific for HCV-RDRP. Such antibodies can be made by known techniques, using the purified enzyme as antigen. Such antibodies bind either r-HCV- RDRP or wild-type HCV-RDRP. The availability of such antibodies makes it possible to prepare an affinity-labeled chromatography matrix for rapid purification of HCV-RDRP. The antibody also makes possible rapid detection of HCV-RDRP in biological materials, for example, in serum of HCV-infected patients.

The invention further provides a method for transfecting a mammalian cell with HCV-RDRP and expressing the enzyme within the cell. Consequently, the invention also provides a transfected mammalian cell line expressing r-HCV-RDRP. Such cells are useful mammalian cell line expressing r-HCV-RDRP. Such cells are useful for assaying the effects of candidate anti-viral compounds as inhibitors of RDRP activity.

Therefore, the invention also provides a method for screening possible inhibitors of RDRP activity in vivo. Compounds with inhibitory activity can have anti-viral activity, since inhibition of the polymerase inhibits viral replication and expression of virus gene products. The in vitro assay is advantageous because it can rule out compounds which cannot enter the infected cell. One class of attractive candidate compounds is the nucleoside analogs; compounds which after being modified (phosphorylated) within cells can bind to substrate sites on the enzyme or which can be incorporated into a newly synthesized RNA but whose presence there disrupts normal function of the HCV polymerase or further replication of an RNA containing the analog. Acyclovir is one example of a very effective and safe nucleoside analogue that inhibits DNA virus replication by inhibiting a viral polymerase (DNA-dependent DNA polymerase) and interfering with primer-template function (chain termination). Such analogs are almost always effective only in the nucleotide triphosphate form. The in vitro assay provides a convenient method of administering the compound in its nucleoside form or nucleoside monophosphate form, allowing endogenous metabolic activity of the cell to convert that form to the active triphosphate, thereby avoiding a step of chemical synthesis of the triphosphate, as would be required for an in vivo assay.

A method for measuring HCV-RDRP activity in vitro is also provided. Such an assay permits identification of the enzyme and evaluation of its concentration during purification. In addition, the assay provides an additional, in vitro, method for screening potential inhibitors of RDRP as candidate anti-viral agents.

In principle, any compound can be tested as a candidate RDRP inhibitor. Certain classes of compounds are considered attractive candidates. These include, without limitation, nucleoside analogs, oligonucleotides and peptides. Certain compounds having planar, polycyclic-aromatic characteristics are also potential inhibitors.

It will be understood that compounds identified as effective RDRP inhibitors must be further screened for toxicity, bioavailability, side effects and the like before being tested as therapeutic agents. Nevertheless, the initial identification as an inhibitor of HCV-RDRP is an essential first step in the development of an anti-viral therapy. It will also be recognized that an inhibitor of r-HCV-RDRP will also inhibit wild-type HCV-RDRP.

In another aspect of the invention, the existence of purified HCV-RDRP or r-HCV-RDRP makes it possible to detect and measure antibodies to RDRP present in the serum of an HCV-infected patient. The fact that such antibodies exist at all is in itself a finding made possible by the expression and preparation of purified r-HCV-RDRP according to the invention. The existence of circulating antibodies to HCV-RDRP in infected serum may be due to lysis of infected cells and release of HCV-RDRP into the extracellular fluids and bloodstream, where it can stimulate an antibody response. As the disease fluctuates in severity, the amounts of HCV-RDRP released and the amounts of antibody thereto would also fluctuate. Therefore, the amount of antibody to HCV-RDRP present in a patient's serum can be used as an indicator, not only of the presence of infection, but of its severity at a given time. The assay for anti-HCV-RDRP can serve as a means of diagnosing infection and also as a means of monitoring the course of the disease over time or in response to treatment. The assay for anti-HCV-RDRP can be carried out by a variety of known techniques, such as the gel separation method described herein. Other suitable methods include ELISA, and radioimmunoassay. A sandwich-type assay, using immobilized r-HCV-RDRP to capture the antibody can then use an anti-immunoglobulin reagent tagged with an appropriate marker such as an enzyme, radioisotope, fluorescent molecule or chemiluminescent marker or the like, all as understood by those skilled in the art. (*Antibodies: A laboratory manual*, Ed Harlow and David Lane, Cold Spring Harbor Laboratory (1988) pp. 553–611.)

FIG. 1. Hepatitis C virus genome and polyprotein cleavage products. The cleavage products of the HCV polyprotein have been tentatively identified using vaccina virus expression systems. The amino terminus of the 5B protein expressed and processed in this system is SMSY (Ser-Met-Ser-Tyr). Although published reports have not proved that the 5B protein has RNA polymerase activity, it does contain the GDD (Gly-Asp-Asp) motif found in other RNA-dependent RNA polymerases. The question has been raised that the 5B protein alone does not encode an active RNA-dependent RNA polymerase enzyme and that another subunit (possibly the NS5A gene product) is essential for catalytic activity. During the initial phases of this work we were unsure if the protein encoded by NS5B would exhibit RNA-dependent RNA polymerase activity simply due to the lack of other essential factors.

Figure 2:
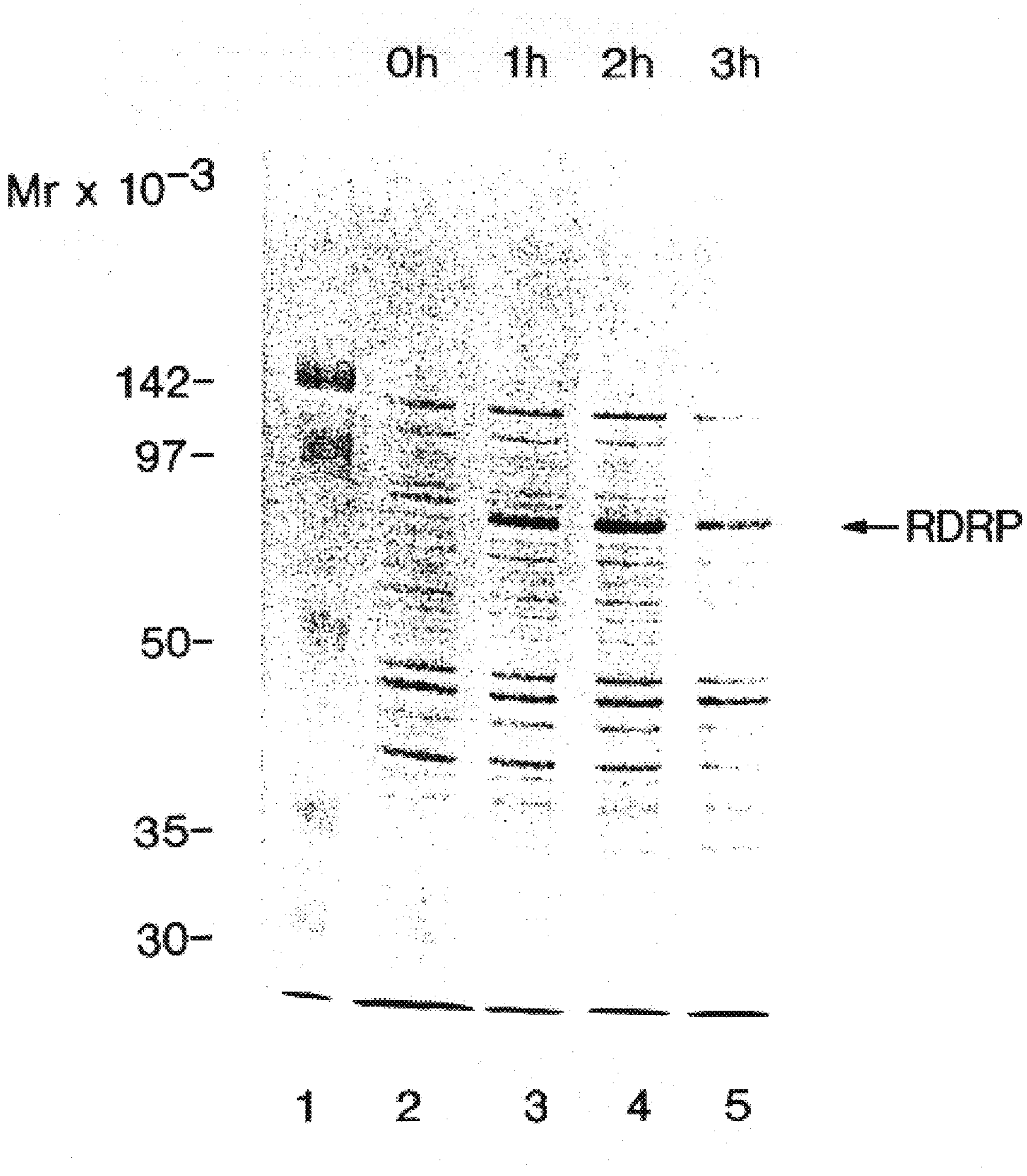

FIG. 2. Expression of r-HCV RNA-dependent RNA polymerase in *E. coli* using the T7 polymerase driven Studier vectors. *E. coli* containing the engineering T7 polymerase driven expression vector were incubated at 37° C. until an $OD_{600}$ of 0.6 was reached. A sample of cells was obtained and IPTG added to a final concentration of 1 mM. Samples were collected at 1, 2 and 3 hours after IPTG induction. Whole cells were lysed in 1× sample buffer at 95° C. and samples analyzed by 10% SDS-PAGE. The photograph shows a representative Coomassie Blue stained gel. Lane 1 represents molecular mass markers; lane 2, the uninduced control (0 h); lane 3, 1 h; lane 4, 2 h; and lane 5, 3 h after IPTG induction. Recombinant r-HCV RNA-dependent RNA polymerase is indicated by an arrow (RDRP).

Figure 3:
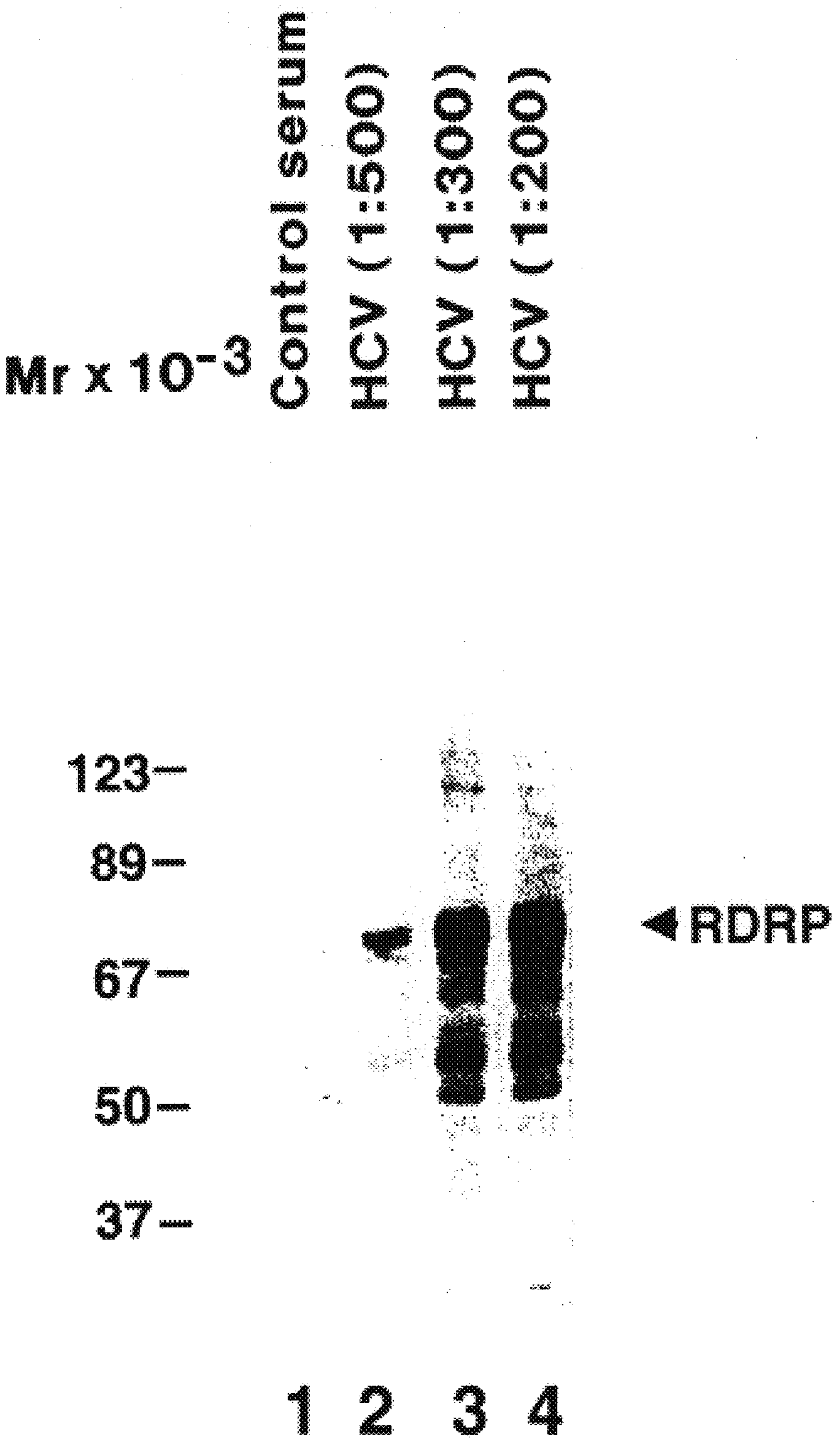

FIG. 3. Some patients with chronic hepatitis C have circulating antibodies that react with recombinant HCV RNA-dependent RNA polymerase. Cells expressing r-HCV RDRP were harvested and lysed by heating in SDS-PAGE sample buffer. Soluble proteins were separated by SDS-PAGE, transferred to nitrocellulose membranes and immunoblotted with human sera using an Immunetics Miniblotter template (Hagedorn, et al. *FEBS Lett.* (1990) 264:59–62). Immunoblots were developed with a secondary anti-human horseradish peroxidase conjugated antibody and enhanced chemiluminescent methods (ECL, Ambersham). This photograph shows an immunoblot where lane 1 was probed with normal human serum and lanes 2 (1:500 dilution), 3 (1:300), and 4 (1:200) were probed with serum from a patient with chronic hepatitis C. The location of recombinant HCV RDRP (visualized by Coomassie and Ponceau S staining) is indicated by an arrow. These lower molecular mass bands seen in lanes 3 & 4 represent proteolytic fragments of RDRP seen when whole *E. coli* lysates are used in immunoblots.

Figure 4:
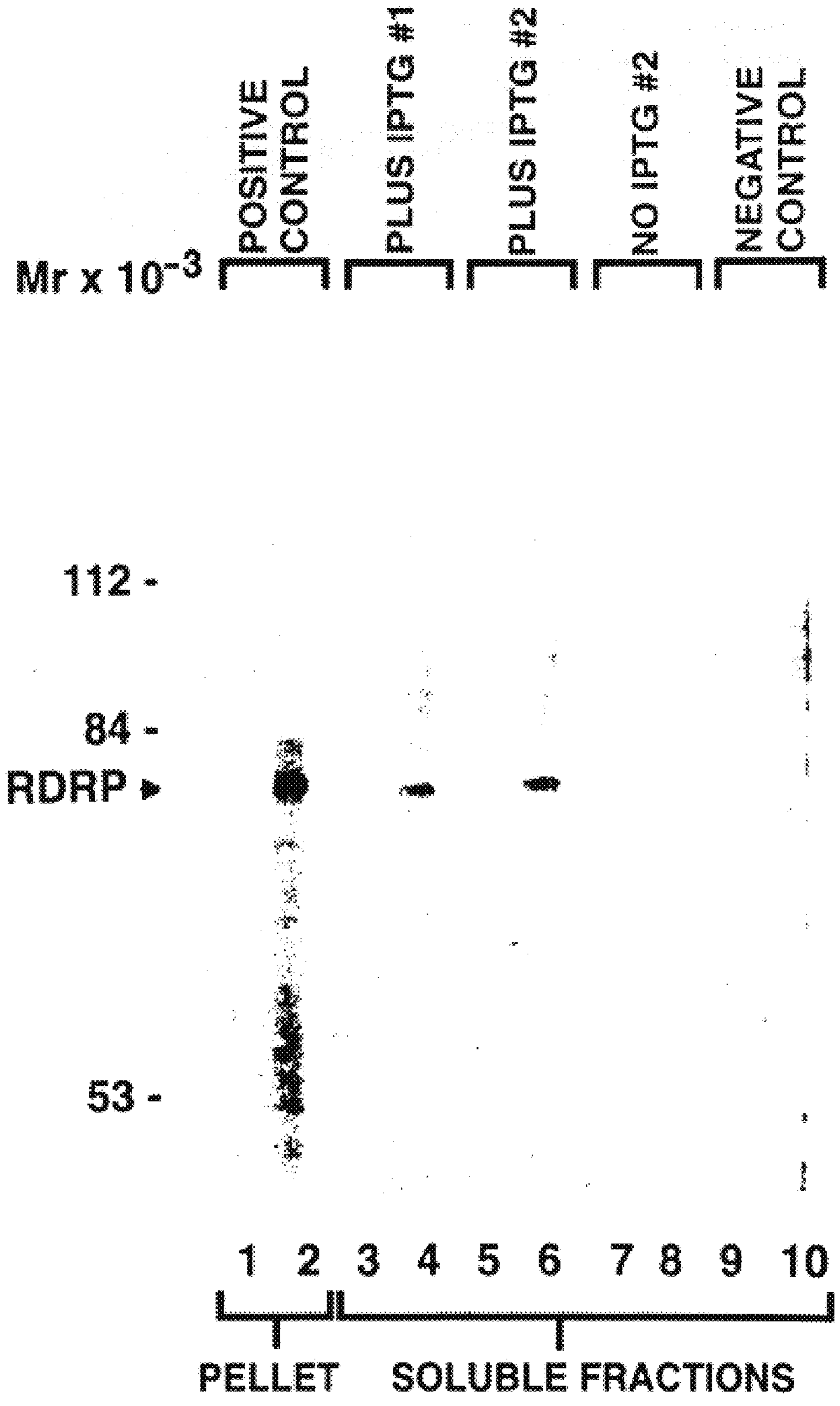

FIG. 4. Solubilization of HCV RDRP under nondenaturing conditions. Cells expressing r-HCV RDRP were harvested and processed using standard methods. Samples of insoluble *E. coli* pellets (pellet, positive control) and soluble fractions from cells containing or not containing (negative control) the RDRP expression vector were separated by SDS-PAGE and transferred to nitrocellulose membranes. Proteins bound to nitrocellulose were probed with rabbit preimmune and rabbit anti-RDRP sera as outlined in FIG. 3. Blots were developed with the ECL system (Amersham). The photograph shows an immunoblot where lanes 1,3,5,7 and 9 were probed with preimmune serum and lanes 2,4,6,8 and 10 were probed with immune serum. Two independently prepared samples of soluble proteins (plus IPTC #1 & #2, lanes 3–6) were examined.

Figure 5:
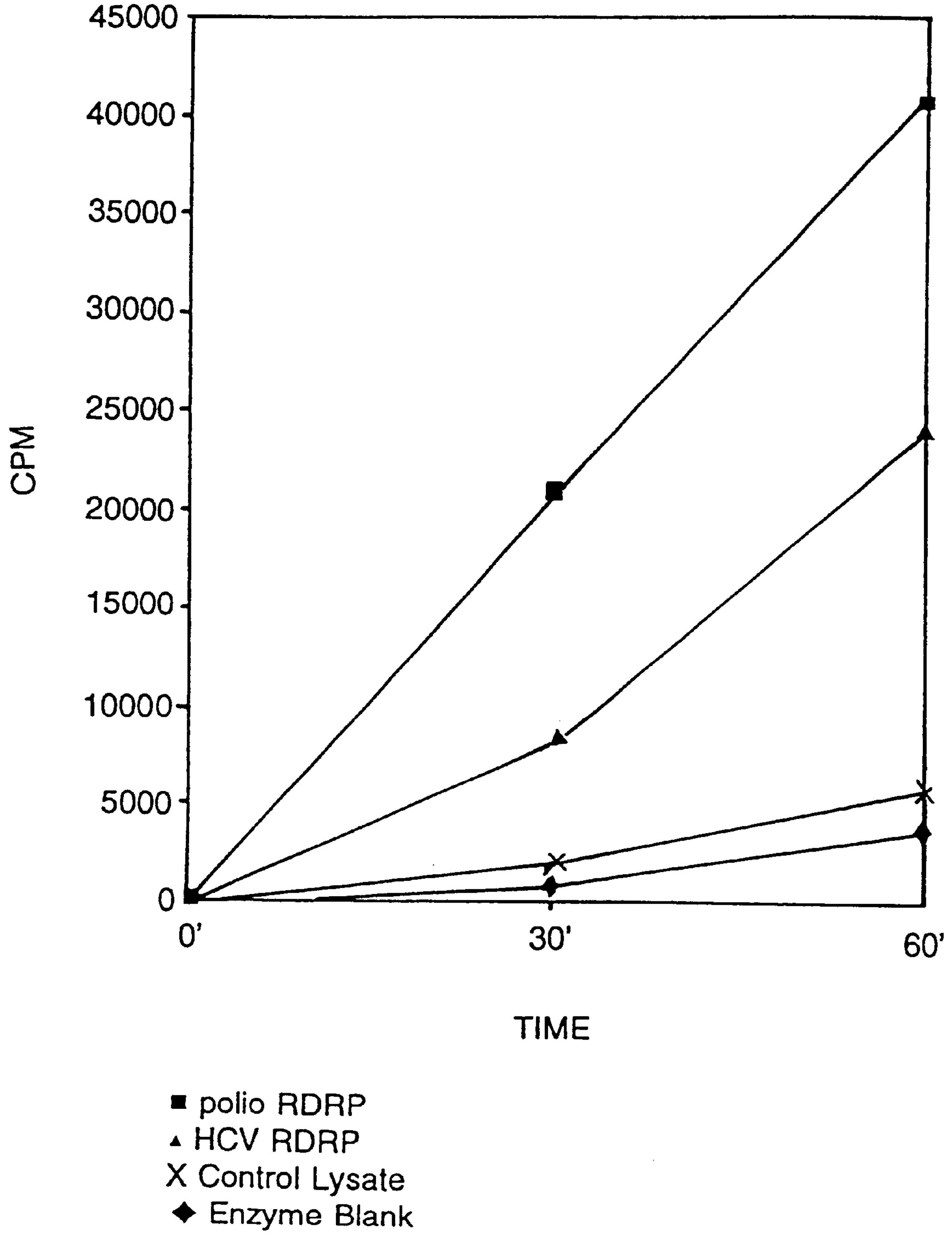

FIG. 5. Enzymatically active recombinant r-HCV RNA-dependent RNA polymerase. Poly(U) polymerase activity of purified recombinant poliovirus RDRP (approximately 50 ng) and equal quantities of soluble protein (approximately 1 $\mu$g) from *E. coli* expressing r-HCV RDRP (HCV RDRP lysate) or control cells not expressing RDRP (control lysate) are shown. Incubations were performed as described previously and CPM of poly (U) recovered from 15 $\mu$l of incubation are shown at 30 min (one sample) and 60 min (mean of duplicates) of incubation are shown (*J. Virol.* (1986) 0 58:790–796).

Figure 6:
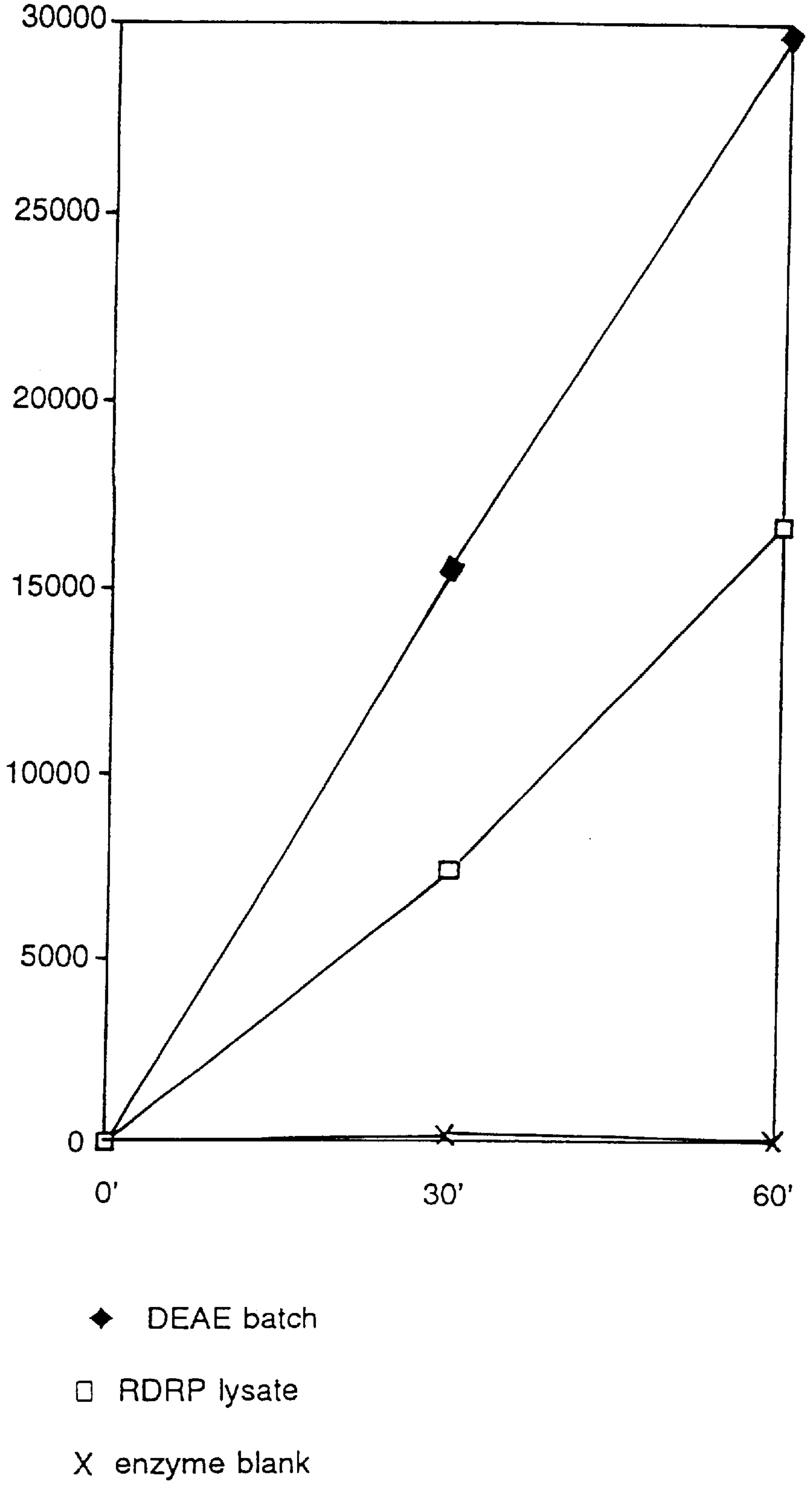

FIG. 6. Enzyme assay of partially purified recombinant HCV RNA-dependent RNA polymerase. Lysates of *E. coli* expressing r-HCV RDRP were prepared and enzyme assays performed as in FIG. 5. The experiment shown used a DEAE resin in a batch purification approach under pH and buffer conditions that allow RDRP to bind the resin. Equal quantities of protein were assayed from cell lysates (designated RDRP lysate) and proteins eluted from DEAE resin with 0.5 M NaCl (designated DEAE batch) that were concentrated to approximately that of the lysate. Additional studies with DEAE resin and other test resins have shown that partial purification of RDRP enzyme activity correlates with increases in the amount of unproteolyzed RDRP that we detect by immunoblotting using rabbit antiserum and the methods outlined in FIG. 4.

Figure 7:
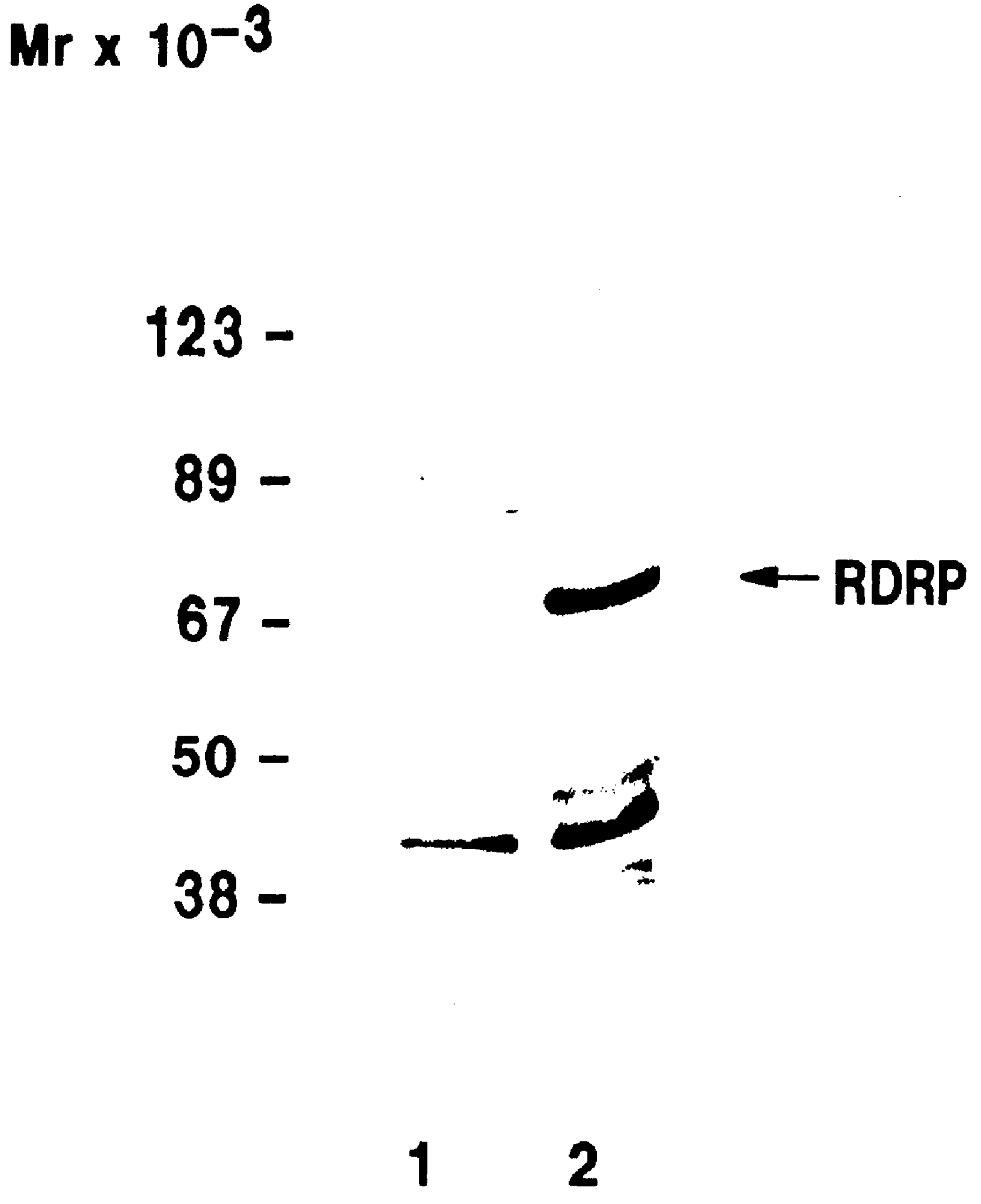

FIG. 7. Immunoaffinity purification of recombinant r-HCV RDRP. This photocopy shows an initial result with an immunoaffinity column prepared with rabbit polyclonal protein A Sepharose purified anti-RDRP antibodies. The starting material was protein solubilized from *E. coli* expressing recombinant r-HCV RDRP. The figure shows an immunoblot of proteins that were eluted from two identical columns that had protein applied under different detergent conditions. Lane 1 depicts proteins eluted from antibody/Sepharose beads that had been mixed overnight with the solubilized recombinant RDRP in 20 mM Tris-pH 7.5, 100 mM KCl, 0.5 mM EdTA, 1 mM DTT, 5% glycerol, and 0.05% Triton X-100. These beads were washed the following morning with 10 mM potassium phosphate buffer-pH 7.2 and proteins eluted with 100 mM glycine-pH 2.5. The eluted protein was collected in 1 M Tris-pH 8.0 to readjust the pH. Proteins eluted from the column were then analyzed by SDS-PAGE and immunoblotting as in FIG. 4. Lane 2 depicts proteins eluted from identical beads mixed with the same starting material except that 0.05% NP-40 was present instead of 0.05% Triton X-100. The location of r-HCV RDRP is indicated.

DETAILED DESCRIPTION OF THE INVENTION

Definitions

"RDRP" stands for RNA-dependent RNA polymerase, an enzyme catalyzing RNA synthesis, the synthesized RNA having a sequence complementary to an RNA template. "HCV-RDRP" is the RDRP of Hepatitis C virus. The modified HCV-RDRP described herein is designated r-HCV-RDRP. The region of the HCV genome designated NS5B has been identified as a protein cleavage product of the HCV polyprotein, using a vaccinia virus expression system as described supra. The nucleotide sequence of NS5B is included in SEQ ID NO:1. Putative amino acid coding by the NS5B sequence begins with nucleotide 7. Where the sequence has been deleted at the 5' end, the remaining sequence has been designated by the nucleotide numbers beginning and ending the remaining coding sequences, not including the stop codon. For example $NS5B_{34-1779}$ designates that part of NS5B including nucleotides 34–1779 of SEQ ID NO:1.

The amino acid sequence encoding the r-HCV-RDRP exemplified herein is given in SEQ ID NO:2. The amino acid sequence encoded by NS5B begins at amino acid No. 3 of SEQ ID NO:2. Where the sequence encoded by NS5B has been deleted at the N-terminus, the remaining sequence is designated $\Delta_n$NS5B where n is the number of amino acids deleted from the N-terminus of NS5B. For example $\Delta^9$ NS5B is the sequence of amino acids 12–593 in SEQ ID NO:2.

Various r-HCV-RDRP constructs are contemplated according to the invention, as described. Modified coding sequences included with the invention have the general sequence ATG-$N_X$-($N^S$) ($N^M$) ($N^S$) ($N^Y$) ($N^S$) ($N^W$) ($N^T$) ($N^G$) ($N^A$)-[$NS5B_{34-1779}$] where $N_X$ is any nucleotoide sequence encoding from 0–20 amino acids, $N^S$ is a codon encoding serine, $N^M$ is a codon encoding methionine, $N^Y$ is a codon encoding tyrosine, $N^W$ is a codon encoding tryptophane, $N^T$ is a codon encoding threonine, $N^G$ is a codon encoding glutamic acid, and $N^A$ is a codon encoding alanine. Any of the codons in parentheses can be deleted, if desired. Up to 5 of the codons in parentheses can be mutated if desired. The term "mutated" is intended to mean altered to encode an amino acid other than that originally encoded by the NS5B sequence. For example, individual codons can be altered to encode alanine, by the known method of alanine scanning mutagenesis. Alanine scanning mutagenesis provides a rapid and convenient method for identifying amino acid positions where substitution is tolerated, without substantially affecting function negatively. Positions where alanine scanning reveals tolerance for substitution are likely to tolerate other amino acid substituents as well. Preferred substituents are one or more histidine residues, which can serve as affinity ligands for metal (e.g. nickel) columns. The presence of histidine provides preferential binding to the column to facilitate purification of r-HCV-RDRP. [$NS5B_{34-1779}$], as defined, represents the nucleotide sequence of the remainder of SEQ ID NO:1, from nucleotides 34–1779, not including the stop codon. The techniques for making any of the foregoing sequences are essentially as described below for the sequence where $N_X$ is GCT and none of the codons in parentheses, encoding the first nine amino acids encoded by NS5B, is deleted. It will be apparent that primers can be synthesized for the desired sequence combined with desired restriction site sequences to facilitate insertion into appropriate expression vectors. The choice of vector is based on factors known in the art, including the host cell, the type of promoter desired and the presence or absence of additional sequences which could be co-expressed with the r-HCV-RDRP. The reaction condition, PCR, vector insertion and host cell growth are as described below or as well-known in the art.

Further modifications can be made to r-HCV-RDRP. A deletion of approximately 25% of the C-terminal region that did not include the Gly-Asp-Asp motif was constructed (r-HCV-RDRP-ΔC) and tested for activity. Although protein was expressed and was detectable by immunoblotting with anti-RDRP serum, lysate of *E. coli* expressing r-HCV-RDRP-ΔC had no measurable activity in either the poly(U) assay or with globin mRNA as template. However, the region of amino acids 565–572 of NS5B (565–574 of SEQ ID NO:2) near the C-terminus is considered to be exposed at the protein surface on the basis of modeling studies. Site directed mutagenesis has been used to alter the coding to Arg 570→His, Arg 572→His and Try 573→His (using the numbering of SEQ ID NO:2). By clustering one or more additional histidine residues in a surface region near one end of the protein, purification by metal-affinity chromatography is facilitated while enzymatic activity is not substantially affected. Other predicted surface regions that can serve as sites for mutagenesis to replace an existing amino acid with histidine include amino acids 47–56, 152–159, 183–184, 210–215, 269–272, 384–391, and 43999–442 in SEQ ID NO:2.

Although the r-HCV-RDRP can be expressed in virtually any host cell type, the enzyme should preferably be in soluble form in order to be useful in in vitro studies, such as testing for inhibitors. When synthesized intracellularly, the enzyme is in an insoluble form in cell lysates unless steps are taken to solubilize the enzyme. In general, host cells are collected and concentrated, then lysed by means known to disrupt the host cells, for example by the use of a host-cell-wall hydrolyzing enzyme, by sonication and the like. In general a protease inhibitor is added to protect against proteolytic enzymes released by cell lysis. A non-ionic detergent can also be employed. Sonicated cells and sub-cellular complexes are subjected to freezing and thawing in the presence of the above-named components. Remaining particulate matter is removed by centrifugation at 10,000–35,000×g. The r-HCV-RDRP remains in the supernatant. A detailed protocol for solubilizing r-HCV-RDRP expressed in *E. coli* is described below.

Further purification of the enzyme is accomplished by techniques and expedients known in the art. These include, but are not limited to, antibody affinity chromatography, metal-binding affinity chromatography (a technique especially suited for modified forms of the enzyme having added histidine residues) as well as conventional ion-exchange columns, differential precipitation with ammonium sulfate and other methods known in the art, not limited to the methods specifically disclosed herein. "Purified form" is used herein to mean any preparation of the enzyme having at least 4-fold greater specific activity than that measured in a solubilized cell lysate.

Antibodies against r-HCV-RDRP can be generated by a variety of known techniques for making monoclonal or polyclonal antibodies. Antibodies to r-HCV-RDRP also bind to HCV-RDRP of infected cells, as shown by the discovery that circulating antibodies to HCV-RDRP are detectable in serum of HCV-infected patients, using r-HCV-RDRP as the antibody ligand. A variety of monoclonal antibodies can be selected, having affinity for different epitopes of r-HCV-RDRP, as known in the art. Some antibodies can be inhibitory of enzyme activity. Others can have a modest affinity that facilitates binding to an antibody-affinity column and subsequent elution under conditions that do not inactivate the enzyme.

Mammalian cells are a preferred host cell for certain purposes, particularly for in vitro screening for inhibitors of HCV-RDRP, and also for developing cell lines that can propagate HCV in cell culture. Any of the known cell lines used for transformation can, in principle, be transformed to express r-HCV-RDRP. Preferred cell lines are those of tissue origin known to be infected by HCV or similar viruses, such as flaviviruses. Such cell lines include, for example, the human macrophage cell line U937, human liver-derived hepG2 cells, and the pig kidney cell line PK15. A recently-discovered segment near the 3'-end of HCV-RNA has a predicted cloverleaf-type secondary structure that is a likely site of interaction for a protein or peptide (which may be host-encoded) that regulates HCV-RDRP (Tanaka, T., et al. (1995) *Biochem. Biophys. Res. Commun.* 215:744,749). Such regulation can take the form of altering the template specificity or the catalytic activity of r-HCV-RDRP as well as the wild-type enzyme. Expression of r-HCV-RDRP in cells that normally express the regulatory protein provides an in vivo cell system where expression of r-HCV-RDRP closely approaches the manner of expression in HCV-infected cells. Also, the presence of active HCV-RDRP in a cell can enhance the replication of HCV introduced by infection or genomic HCV RNA introduced by transfection, by providing a "jump start" for HCV replication. Most importantly, the ability to measure r-HCV-RDRP activity in transformed cells provides an essential key to screening potential inhibitors of HCv-RDRP for their ability to inhibit the enzyme in vivo.

Assay for RNA synthesis by r-HCV-RDRP in vitro has demonstrated that the enzyme can catalyze synthesis of poly(U) using a poly(A) template, and synthesis of RNA, using a globin mRNA template. Both reactions were >90% primer-dependent under the described reaction conditions. The enzyme had no detectable activity in the absence of $Mg^{++}$ and showed maximal activity in the presence of about 20 mM $Mg^{++}$. A method for screening compounds that have anti-viral activity is provided by testing the effect of various compounds on the RDRP enzyme activity in vitro. The in vitro method includes comparing the amounts of RNA synthesized in the presence and absence of a test compound. An inhibitory effect is indicated if the amount of RNA synthesized is reduced in a reaction where the test compound is present compared to a control reaction where the test compound is absent.

The stably transfected cell line expressing r-HCV-RDRP is especially useful for carrying out in vivo screening for compounds that inhibit the polymerase in intact mammalian cells. Such inhibitors are likely inhibitors of HCV replication in infected cells. An in vivo test is advantageous since it can screen out cytotoxic compounds, and compounds that cannot enter the cell in sufficient quantity. It also provides the added capability of testing compounds which are precursors of the actual inhibitor but converted to inhibitor by the cells metabolic processes. Examples of precursor inhibitors include nucleoside analogs which must be phosphorylated to be converted to active inhibitor, and compounds having an active group protected by a linkage that undergoes hydrolytic cleavage, intracellularly, to form active inhibitor. Non-nucleoside analogs having the general structure shown are considered attractive candidates for r-HCV-RDRP inhibitors

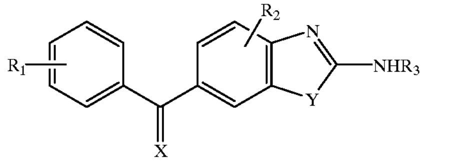

where $R_1$ and $R_2$ are alkyl, amino, hyrodxy, alkoxy or halo groups, $R_3$ is an alkyl, aryl, hydroxy or alkoxy group, X is O, $NR_3$, O, $CH_2$ or $CHR_3$. In general, the test cells additionally are transformed with a reporter construct whose expression requires the action of r-HCV-RDRP, or whose expression is amplified by the presence of r-HCV-RDRP. Reporter genes are well known in the art, including, but not limited to luciferase, secreted alkaline phosphatase and the fluorescent green protein, all of which are commercially available. An attractive strategy is to use an antisense gene for the reporter, that is, a version of the reporter gene which expresses an antisense, or (−) strand messenger RNA of the reporter gene. Activity of an RDRP is then required to produce a sense (+) strand in RNA which can be translated to yield active reporter. This system has the advantage that there is no background level of reporter activity in the absence of active HCV-RDRP, if the RDRP is inhibited. An outline for the construction of suitable (−) strand reporter gene is set forth below.

Subcloning of the HCV NS5B region—PCR-primers for the amplification of the NS5B-region were designed based on the N-terminus as predicted by vaccinia virus expression studies (Lin, C. et al. (1994) supra; Grakoui, A. et al. (1993) supra) and the C-terminus based on the end of the open-reading-frame of the HCV poly protein (Choo, Q-L. et al. (1991) supra). The template was the original prototype HCV (type la) clone (obtained from the CDC) (Choo, Q-L. et al. (1989), (1991), supra). Using the following primers, 5'-ATA GCT AGC ATG TCT TAC TCT TGG ACA GG-3' (SEQ ID NO:3) and 5'-ATA GGA TCC TCA TCG GTT GGG GAG GAG G-3' (SEQ ID NO:4), we amplified the NS5B-region with minimum changes at the N-terminus (ASMSY SEQ ID NO:5 instead of SMSY SEQ ID NO:7) and directionally cloned it into pET-11a (Novagen) at NheI and BamHI restriction sites (Maniatis et al. (1982) *Molecular Cloning,* Cold Spring Harbor Laboratory, Plainview, N.Y.). The PCR amplified gene had a NheI site engineered into the 5' end and a BamHI site at the 3' end. This construct results in the synthesis of a recombinant protein with an amino terminal sequence of MASMSY rather than the SMSY amino terminus of the putative wild-type NS5B protein predicted by vaccinia virus expression studies.

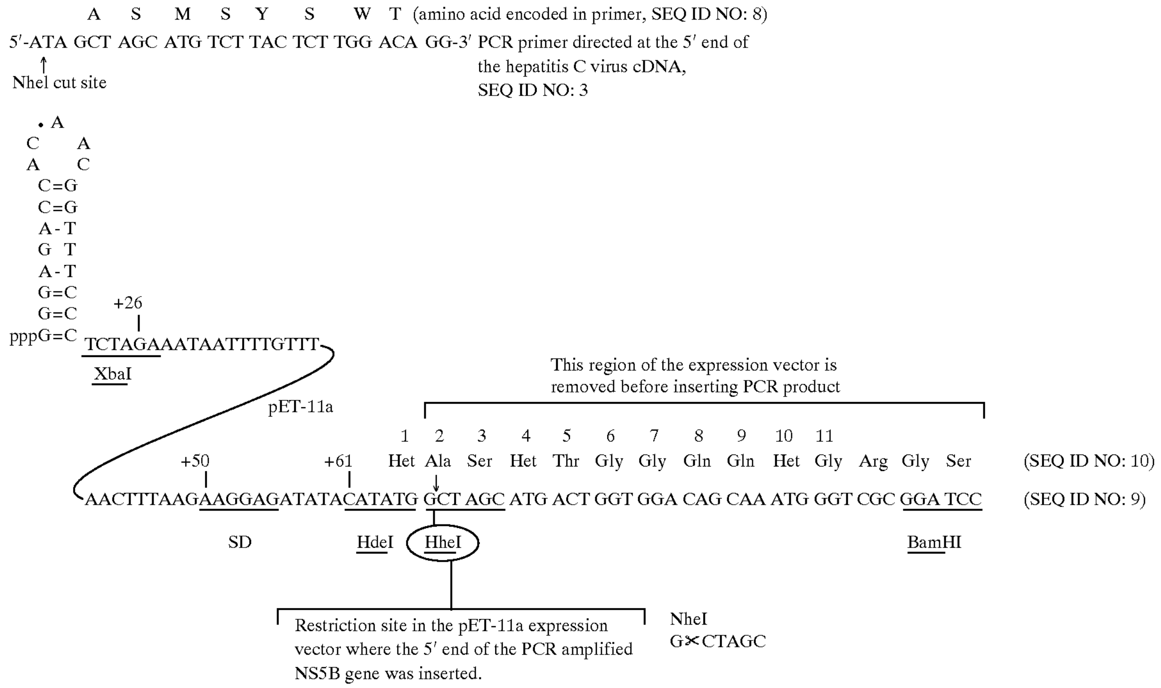

Material and Methods

Material—All chemicals were purchased from Fisher and all enzymes from Gibco BRL unless stated otherwise. AmpliTaq was purchased from Perkin-Elmer. All other PCR and ligation components were from Invitrogen. Lysozyme, antibiotics, and pre-stained protein standards were from Sigma. Nucleotides and poly(A) were from Pharmacia. [$^3$H-]UTP was from Dupont NEN. Oligo(U) was a generous gift from E. Ehrenfeld (University of California, Irvine).

The PCR reaction was preceded by an 2 min incubation at 94° C., followed by 20 cycles of 1 min 94° C., 2 min 55° C., and 3 min 72° C. (Coy Corporation Tempcycler II). Reactions were completed by keeping the temperature at 72° C. for another 7 min and subsequent cooling to 4° C. Amplified DNA was purified by phenol/chloroform extraction, digested with NheI and BamHI and re-purified using phenol/chloroform extraction and ethanol precipitation.

Insert and vector were ligated overnight at 14.5° C. at an 3:1 ratio (insert:vector) using T4-ligase (Maniatis, supra). Ligated material was used to transform *E. coli* (Top10™ from Invitrogen) using $CaCl_2$ methods. Colonies were selected on ampicillin plates and minipreps of plasmid DNA isolated from single colonies were characterized using restriction enzyme analyses. Plasmid DNA obtained by mini-preparation methods was used to transform BL21 (λDE3) *E. coli* (Novagen), organisms containing plasmid were selected using ampicillin and mini-preparations of plasmid DNA from single colonies were analyzed by restriction enzyme digestion.

Expression, purification and solubilization of the putative HCV RDRP-BL21 (λDE3) *E. coli* containing the pET-11a-NS5B construct described above were grown in overnight cultures (M9ZB media with Carbenicillin) and diluted 1:20 into fresh medium the next morning. Cells were incubated at 37° C. until the culture media reached an $OD_{600}$ of 0.6. IPTG was added at that time to a final concentration of 1 mM. Expression of the putative RDRP was followed by SDS-PAGE analysis of whole cells lysed in sample buffer at 90° C.

To solubilize RDRP under non-denaturing conditions cells were harvested 2 h after IPTG-induction. RDRP was solubilized by lysing the cells on ice for 20 min in 20 mM Tris pH 7.5, 100 mM KCl, 0.5 mM EDTA, 1 mM DTT, 0.1% Trition X-100 and 30 μg/ml lysozyme. Samples were sonicated on ice with an 0.5 inch probe (pulse setting) for 5 min (Ultrasonics Inc. W-225, output-setting 7) and centrifuged (19,000 g at 4° C. for 30 min). The insoluble fraction (pellet) obtained from these preparations was enriched with RDRP. Pellets were suspended in SDS-PAGE sample buffer and heated for 10 min at 90° C. and used as RDRP markers for SDS-PAGE gels. However, active enzyme was found in the supernatant, as set forth in the following protocol.

Outline of Solubilization Method for Recombinant RDRP

1. Thaw 5 g of *E. coli* pellet.
2. Resuspend 5 g of pellet in:

| | |
|---|---|
| 45 ml | Lysis buffer |
| 40 μl | 100 mM PMSF (plus other protease inhibitors) |
| 150 μl | lysozyme (10 mg/ml) |

Lysis buffer
- 20 mM tris pH 7.5 (at 4° C.)
- 0.5 mM EDTA
- 100 mM KCl
- 1 mM DTT
- 0.1% Triton X-100 (or 0.1% NP-40)
- 10.0% (v/v) Glycerol 3. Place samples on ice for 20 min, then sonicate for 5 min (pulse mode; setting between 6–7). Mix while sonicating.
4. After sonicating flash freeze the lysate in liquid nitrogen (put the lysate into liquid nitrogen for about 1–2 min).
5. Quickly thaw the lysate at 370° C. water bath.
6. Sonicate the lysate for 1 min.
7. Add an additional 5 ml of lysis buffer per 45 ml of sonicated sample mix.
8. Divide entire sonicated sample into 50 ml fractions (Fisher 50 ml tubes).
9. Centrifuge lysate at 12,500 rpm for 20 min in Beckman J-17 rotor (or 12,500 rpm in a Sorvall SS-34 rotor).
10. Remove supernatants to clean (sterile) 50 ml Fisher tubes and add sterile protein grade glycerol to a final concentration of 10% (for example, 4.44 ml of glycerol/40 ml of supernatant). This solution is stored at 4° C. and used as starting material for the purification of enzymatically active HCV RDRP.

Further purification is accomplished by employing the following steps, either singly or in combination.

Soluble proteins from lysate of *E. coli* expressing recombinant HCV RDRP (10,000 × g supernatant)
↓
45% ammonium sulfate precipitated proteins (subsequently dialyzed in Tris-pH 7.5 with 10% glycerol and 1 mM DTT)
↓
DEAE anion exchange chromatography (starting material applied at pH 8.5 - Tris buffer, wash step with same buffer and enzyme is eluted with a 0–0.5 M NaCl gradient)
↓
Phosphocellulose chromatography (concentrated DEAE fractions containing enzyme are diluted to decrease salt concentration and change pH to 8.0 (Tris/HCl) before applying samples to column, wash step, and elution with a 0–0.5 M NaCl gradient)
↓
FPLC gel filtration chromatography (Superose 12 HR 10/30 - Pharmacia) (starting material is concentrated, buffer changed to 150 mM NaCl with Tris pH 8.0 and applied in a 200 μl volume with a flow rate of 0.3 ml/min)
↓
Recombinant HCV RDRP for enzyme assays (stored in aliquots at −70° C. with Tris-pH 8.0, 100 mM NaCl, 20% glycerol, 0.1% NP-40, & 1 mM DTT)

As in all protein purification procedures, one can modify buffers, pH and other conditions to further optimize the purification of HCV RDRP. An additional final purification step (or substitution for the FPLC gel filtration step) is a Mono-S cation exchange chromatography step at pH 6.0 with a MES buffer (the isoelectric point of the enzyme is approximately 8.8). All purification steps are monitored for enzyme activity using RDRP assay, total protein, and analyzed by SDS-PAGE.

Rabbit anti-HCV RDRP serum—RDRP solubilized from the pellet fraction as described above was separated by preparative SDS-PAGE and used to immunize rabbits. Animals were immunized at 4–5 week intervals as described in detail previously. (Harlow, E. and D. Lane (1988) *Antibodies: A laboratory manual,* Cold Spring Harbor Laboratory, pp. 553–611.)

Immunoblotting analysis—Immunoblots were performed using previously described methods with the modification that secondary HRP conjugated antibodies were used with the enhanced chemiluminescent system (ECL, Amersham). When rabbit serum was the primary antibody, the secondary antibody was anti-rabbit immunoglobulin. When human serum was screened the secondary antibody was anti-human immunoglobulin. Serum from patients with documented chronic hepatitis C infections was provided by Dr. Michael Beach of the Centers for Disease Control and Prevention (Atlanta).

Poly(U) polymerase assay—Enzyme activity in soluble fractions was measured using a poly(U) polymerase assay with poly(A) as template and oligo(U) as a primer (Hey, T. D. et al. (1986) *J. Virol.* 58:790–796). Samples (generally 2 μl) were assayed in 50 μl incubations containing 50 mM HEPES (pH 8.0), 500 μM each ATP, CTP, and GTP; 4 mM DTT, 3 mM $MgAc_2$; and 60 μM ZnCl2. [$^3$H]UTP at a concentration of 15 μM (specific activity: 27 Ci/mol) was also present. Each incubation contained 1 μg of poly(A) and 0.5 μg oligo(U) as a primer.

Incubation were at 30° C. for 30–60 min, [$^3$H]poly(U) was precipitated with TCA in the presence of carrier DNA and collected on Whatman GF/C filters. Filters were washed with 0.1 M sodium pyrophosphate/1 N Hydrochloric acid and 95% ethanol, respectively. [$^3$H]poly(U) was quantitated by liquid scintillation spectrometry (LKB 1218 RackBeta).

Stable Transfection of Baby Hamster Kidney (BHK) Cells Using Lipofectin

Day 1 (Afternoon)

Split the BHK cells into 6 well plates aiming for 50% confluence for transfection Day 2 (After 4 P.M.)

Prepare the following solutions in sterile tubes:

(A) 50 $\mu$l miniprep DNA+50 $\mu$l media without serum (DMEM/F12) (2 each)

(B) 6.25 $\mu$l Lipofectin (Life Technologies, Gaithersburg, MD)+93.75 $\mu$l media (C) 12.5 $\mu$l Lipofectin+87.5 $\mu$l media (D) 6.25 $\mu$l Lipofectin+193.75 $\mu$l media (mock transfection)

(E) 12.5 $\mu$l Lipofectin+187.5 $\mu$l media (mock transfection)

Gently mix A&B and A&C and let the DNA and Lipofectin react for 15 minutes at room temperature. During this time, wash the cell twice with 2 mls of DMEM/F12. Add 1.8 mls of DMEM/F12 to the DNA/Lipofectin complex and add it to the cells with gentle swirling. Leave the cells in the incubator overnight.

Day 3 (9 A.M.)

Remove the DNA/Lipofectin and add 3 mls of media+serum to the cells. Incubate the cells for 30–48 hours. Split the cell 1:20, 1:50 and 1:100 into 10 cm dishes in 10 mls of media+serum containing 600 $\mu$g/ml geneticin. Allow 3–7 days for selection and 10–14 days for colony formation. The same protocol can be adapted to employ Starburst Dendrimer (Life Technologies, Gaithersburg, Md.) instead of Lipfectin, to improve transfection efficiency. After selection, ring clone colonies onto 24 well plates and assay media from confluent wells for RDRP activity. Maintain cells n 600 $\mu$g/ml geneticin.

Use of Stably Transfected Cells Expression HCV RDRP to Identify Compounds that Enter Intact Cells and Inhibit HCV RDRP The most direct approach to determining the effect of potential inhibitors of HCV RDRP in transformed cells is to directly measure RDRP activity in cell extracts after cells have been incubated with compounds and washed extensively. This can be done using the RDRP assay described herein (with a HCV template) and requires no other new development except the cell-line. In brief, cells are incubated under conditions that maximally express active enzyme and in sufficient quantities for subsequent enzyme assays. Test compounds are added to incubations, media are removed at the desired time and cells are extensively washed to remove extracellular test compounds. Extracts of cells are prepared for RDRP assays following the general methods described herein. This approach is relatively rapid and requires only moderate changes in our current methods (new cell-lines). Duplicate incubations are performed if kinetic studies of inhibitors need to be done in intact cells (how rapid does inhibition occur in cells). The only potential problem with this approach might be contamination of cell lysates with a compound that does not enter cells but contaminates lysates during their preparation. Precautions to avoid this possible problem are taken and include studies to determine what the optimal "washing" procedure will be. The major advantage of this system is that compounds that may require labor intensive modifications (phosphorylation of nucleosides) for testing with purified RDRP are rapidly screened. A more rapid screening can be achieved by transiently transfecting cells that have been incubated with potential inhibitors with a plasmid engineered to express an HCV RNA template that also encodes an easily measured reporter molecule (such as secreted alkaline phosphatase or luciferase). Such a system measures HCV RDRP activity in intact cells (concentrations of inhibitions would not be diluted by lysing cells, etc. Cells in which RDRP activity is inhibited can be rapidly screened, so that large numbers of candidate inhibitors can be screened rapidly.

A reporter system has been devised whereby activity of r-HCV-RDRP expressed in a host cell is required for expression of a reporter gene. The host cell is transfected with a construct designed to carry the reporter coding sequence in antisense form in a structure that models the HCV replicative intermediate, when expressed as mRNA. The mRNA has, starting from the 5' end, a cap site, the reporter coding region in the antisense, (−) strand, form, an HCV internal ribosome entry site (IRES) element, also in (−) strand form, a ribozyme sequence in (+) strand form, and a polyadenylation site in (+) strand form. Such an mRNA, if translated, would give rise to a nonsense protein, encoded from the (−) strand of the reporter gene. However, if the complementary strand is synthesized by r-HCV-RDRP, the coding sequence of the (+) strand is translatable as the reporter protein (e.g., luciferase, fluorescent green protein, secreted alkaline phosphatase, etc.). The complement produced by RDRP lacks a capped 5' end, since the complement synthesis occurs in the cytoplasm and capping occurs in the host cell nucleus. However, the presence of the HCV-IRES element allows cap-independent translation. (The IRES element will be situated 5' to the (+) strand coding sequence in the complementary strand). The function of the ribozyme motif is to remove the polyA tail from the 3' end of the (−) strand, and incidentally to remove itself as well, prior to complementary strand synthesis by RDRP. A suitable ribozyme motif is provided, for example, by the $R_289_{CC}$ ribozyme of hepatitis delta virus. As transcribed from an integrated DNA, the reporter in RNA can be diagrammed as

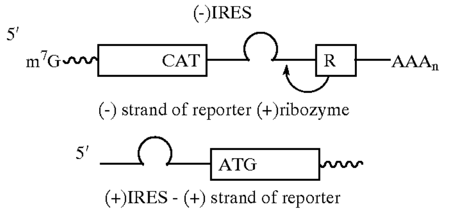

Additions to the foregoing structure include providing a sequence of the HCV 3' untranslated region, which provides a secondary structure that can regulate or enhance r-HCV-RDRP activity. The action of r-HCV-RDRP permits expression of the reporter gene, such that a readily identifiable reaction product such as fluorescence, chemiluminescence or dye generation reaction. The presence of such reaction products indirectly indicates the activity of the r-HCV-RDRP expressed in the host cell and therefore provides a means for observing the effects of a test compound on r-HCV-RDRP activity, in vivo. Inhibitors of in vivo r-HCV-RDRP activity are potential anti-viral agents against HCV.

While the invention has been disclosed in detail with respect to certain specific embodiments and examples, it will be understood that further embodiments, examples and modifications made according to one or more of the teachings, principles and results disclosed herein, combined with knowledge in the art as applied by a person of ordinary skill therein all fall within the scope of the invention.

What is claimed is:

1. A method for modifying NS5B protein of hepatitis-C virus (HCV), said NS5B protein having N-terminal amino acids lacking an N-terminal methionine, comprising the steps of:

(a) adding to the N-terminus of said protein a peptide of from 1–20 amino acids, said peptide having an N-terminal methionine, (b) deleting up to 9 N-terminal amino acids of said NS5B protein, (c) substituting an amino acid for any of 1–5 amino acids within the first 9 N-terminal amino acids of said NS5B protein.

said steps being carried out in the alternative or in any combination that provides a modified NS5B protein having an N-terminal methionine.

2. The method of claim 1 wherein the substituting amino acid of step (c) is alanine.

3. The method of claim 1 wherein the substituted amino acid of step (c) is histidine.

4. The method of claim 1 wherein the peptide of step (a) is a polyalanine having an N-terminal methionine.

5. The method of claim 1 wherein the peptide of step (a) comprises a specific proteolytic cleavage site.

* * * * *

UNITED STATES PATENT AND TRADEMARK OFFICE

CERTIFICATE OF CORRECTION

PATENT NO. : 6,248,589 B1
DATED : June 19, 2001
INVENTOR(S) : Hagedorn et al.

It is certified that error appears in the above-identified patent and that said Letters Patent is hereby corrected as shown below:

Title page,
Under "OTHER PUBLICATIONS", please replace "Kuo, G. et a. "An
Assay for Circulating Antibodies to a Major Etilogic Virus of Human Non-A, Non-B Hepatitis"" with -- Kuo, G. et al. "An Assay for Circulating Antibodies to a Major Etiologic Virus of Human Non-A, Non-B Hepatitis" --.

In the first column, under "OTHER PUBLICATIONS", please replace "Choo, Q.-L et a." with – Choo, Q.-L. et al. --.

In the second column, under "OTHER PUBLICATIONS", please replace " "Complex Synthetic
ChemicalLibraries indexed with Molecular Tags" " with – "Complex Synthetic Chemical Libraries indexed with Molecular Tags" --.

In the second column, under "OTHER PUBLICATIONS", please replace " "A Novel Sequence Found at the 3'Terminus of Hepatitis C Virus Genome" " with "A Novel Sequence Found at the 3' Terminus of Hepatitis C Virus Genome" --.

In the second column, below "OTHER PUBLICTIONS", before Attorney, Agent or Firm, please delete "(74)".

In the second column, below "OTHER PUBLICATIONS", just after Attorney, Agent or Firm, please delete "(57)".

Column 5,
Line 21, replace "IPTC" with – IPTG --.

Column 6,
Line 29, replace "$\Delta n$" *with* -- $\Delta^n$ --.

Column 7,
Line 29, replace "43999-442" with – 439-442 --.

Columns 9 and 10,
Line 45 (approximately), in SEQ ID NO: 10, change three occurrences of "Het" to three occurrences of – Met --.

UNITED STATES PATENT AND TRADEMARK OFFICE

CERTIFICATE OF CORRECTION

PATENT NO. : 6,248,589 B1
DATED : June 19, 2001
INVENTOR(S) : Hagedorn et al.

It is certified that error appears in the above-identified patent and that said Letters Patent is hereby corrected as shown below:

Column 11,
Line 52, replace "370°C" with -- 37°C --.

Column 14,
Line 15, replace "strand, form" with -- strand form --.

Signed and Sealed this

Twenty-seventh of November, 2001

*Attest:*

Nicholas P. Godici

NICHOLAS P. GODICI

*Attesting Officer*

*Acting Director of the United States Patent and Trademark Office*

UNITED STATES PATENT AND TRADEMARK OFFICE

CERTIFICATE OF CORRECTION

PATENT NO. : 6,248,589 B1
DATED : June 19, 2001
INVENTOR(S) : Hagedorn et al.

It is certified that error appears in the above-identified patent and that said Letters Patent is hereby corrected as shown below:

Column 1,
Line 8, insert the following paragraph before heading "FIELD OF THE INVENTION."

-- ACKNOWLEDGEMENT OF FEDERAL RESEARCH SUPPORT

This invention was made with government support under contract numbers AI041424 and CA044568 awarded by the National Institutes of Health. The government has certain rights in the invention. --.

Signed and Sealed this

Second Day of May, 2006

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 1788
<212> TYPE: DNA
<213> ORGANISM: Hepatitis C virus
<220> FEATURE:
<221> NAME/KEY: CDS
<222> LOCATION: (1)..(1782)

<400> SEQUENCE: 1

atg gct agc atg tct tac tct tgg aca ggc gca ctc gtc acc ccg tgc       48
Met Ala Ser Met Ser Tyr Ser Trp Thr Gly Ala Leu Val Thr Pro Cys
  1               5                  10                  15

gcc gcg gaa gaa cag aaa ctg ccc atc aat gca cta agc aac tcg ttg       96
Ala Ala Glu Glu Gln Lys Leu Pro Ile Asn Ala Leu Ser Asn Ser Leu
             20                  25                  30

cta cgt cac cac aat ttg gtg tat tcc acc acc tca cgc agt gct tgc      144
Leu Arg His His Asn Leu Val Tyr Ser Thr Thr Ser Arg Ser Ala Cys
         35                  40                  45

caa agg cag aag aaa gtc aca ttt gac aga ctg caa gtt ctg gac agc      192
Gln Arg Gln Lys Lys Val Thr Phe Asp Arg Leu Gln Val Leu Asp Ser
     50                  55                  60

cat tac cag gac gta ctc aag gag gtt aaa gca gcg gcg tca aaa gtg      240
His Tyr Gln Asp Val Leu Lys Glu Val Lys Ala Ala Ala Ser Lys Val
 65                  70                  75                  80

aag gct aac ttg cta tcc gta gag gaa gct tgc agc ctg acg ccc cca      288
Lys Ala Asn Leu Leu Ser Val Glu Glu Ala Cys Ser Leu Thr Pro Pro
                 85                  90                  95

cac tca gcc aaa tcc aag ttt ggt tat ggg gca aaa gac gtc cgt tgc      336
His Ser Ala Lys Ser Lys Phe Gly Tyr Gly Ala Lys Asp Val Arg Cys
            100                 105                 110

cat gcc aga aag gcc gta acc cac atc aac tcc gtg tgg aaa gac ctt      384
His Ala Arg Lys Ala Val Thr His Ile Asn Ser Val Trp Lys Asp Leu
        115                 120                 125

ctg gaa gac aat gta aca cca ata gac act acc atc atg gct aag aac      432
Leu Glu Asp Asn Val Thr Pro Ile Asp Thr Thr Ile Met Ala Lys Asn
    130                 135                 140

gag gtt ttc tgc gtt cag cct gag aag ggg ggt cgt aag cca gct cgt      480
Glu Val Phe Cys Val Gln Pro Glu Lys Gly Gly Arg Lys Pro Ala Arg
145                 150                 155                 160

ctc atc gtg ttc ccc gat ctg ggc gtg cgc gtg tgc gaa aag atg gct      528
Leu Ile Val Phe Pro Asp Leu Gly Val Arg Val Cys Glu Lys Met Ala
                165                 170                 175

ttg tac gac gtg gtt acc aag ctc ccc ttg gcc gtg atg gga agc tcc      576
Leu Tyr Asp Val Val Thr Lys Leu Pro Leu Ala Val Met Gly Ser Ser
            180                 185                 190

tac gga ttc caa tac tca cca gga cag cgg gtt gaa ttc ctc gtg caa      624
Tyr Gly Phe Gln Tyr Ser Pro Gly Gln Arg Val Glu Phe Leu Val Gln
        195                 200                 205

gcg tgg aag tcc aag aaa acc cca atg ggg ttc tcg tat gat acc cgc      672
Ala Trp Lys Ser Lys Lys Thr Pro Met Gly Phe Ser Tyr Asp Thr Arg
    210                 215                 220

tgc ttt gac tcc aca gtc act gag agc gac atc cgt acg gag gag gca      720
Cys Phe Asp Ser Thr Val Thr Glu Ser Asp Ile Arg Thr Glu Glu Ala
225                 230                 235                 240

atc tac caa tgt tgt gac ctc gac ccc caa gcc cgc gtg gcc atc aag      768
Ile Tyr Gln Cys Cys Asp Leu Asp Pro Gln Ala Arg Val Ala Ile Lys
                245                 250                 255
```

-continued

```
tcc ctc acc gag agg ctt tat gtt ggg ggc cct ctt acc aat tca agg      816
Ser Leu Thr Glu Arg Leu Tyr Val Gly Gly Pro Leu Thr Asn Ser Arg
            260                 265                 270

ggg gag aac tgc ggc tat cgc agg tgc cgc gcg agc ggc gta ctg aca      864
Gly Glu Asn Cys Gly Tyr Arg Arg Cys Arg Ala Ser Gly Val Leu Thr
        275                 280                 285

act agc tgc ggt aac acc ctc act tgc tac atc aag gcc cgg gca gcc      912
Thr Ser Cys Gly Asn Thr Leu Thr Cys Tyr Ile Lys Ala Arg Ala Ala
    290                 295                 300

tgt cga gcc gca ggg ctc cag gac tgc acc atg ctc gtg tgt ggc gac      960
Cys Arg Ala Ala Gly Leu Gln Asp Cys Thr Met Leu Val Cys Gly Asp
305                 310                 315                 320

gac tta gtc gtt atc tgt gaa agc gcg ggg gtc cag gag gac gcg gcg     1008
Asp Leu Val Val Ile Cys Glu Ser Ala Gly Val Gln Glu Asp Ala Ala
                325                 330                 335

agc ctg aga gcc ttc acg gag gct atg acc agg tac tcc gcc ccc ccc     1056
Ser Leu Arg Ala Phe Thr Glu Ala Met Thr Arg Tyr Ser Ala Pro Pro
            340                 345                 350

ggg gac ccc cca caa cca gaa tac gac ttg gag ctc ata aca tca tgc     1104
Gly Asp Pro Pro Gln Pro Glu Tyr Asp Leu Glu Leu Ile Thr Ser Cys
        355                 360                 365

tcc tcc aac gtg tca gtc gcc cac gac ggc gct gga aag agg gtc tac     1152
Ser Ser Asn Val Ser Val Ala His Asp Gly Ala Gly Lys Arg Val Tyr
    370                 375                 380

tac ctc acc cgt gac cct aca acc ccc ctc gcg aga gct gcg tgg gag     1200
Tyr Leu Thr Arg Asp Pro Thr Thr Pro Leu Ala Arg Ala Ala Trp Glu
385                 390                 395                 400

aca gca aga cac act cca gtc aat tcc tgg cta ggc aac ata atc atg     1248
Thr Ala Arg His Thr Pro Val Asn Ser Trp Leu Gly Asn Ile Ile Met
                405                 410                 415

ttt gcc ccc aca ctg tgg gcg agg atg ata ctg atg acc cat ttc ttt     1296
Phe Ala Pro Thr Leu Trp Ala Arg Met Ile Leu Met Thr His Phe Phe
            420                 425                 430

agc gtc ctt ata gcc agg gac cag ctt gaa cag gcc ctc gat tgc gag     1344
Ser Val Leu Ile Ala Arg Asp Gln Leu Glu Gln Ala Leu Asp Cys Glu
        435                 440                 445

atc tac ggg gcc tgc tac tcc ata gaa cca ctt gat cta cct cca atc     1392
Ile Tyr Gly Ala Cys Tyr Ser Ile Glu Pro Leu Asp Leu Pro Pro Ile
    450                 455                 460

att caa aga ctc cat ggc ctc agc gca ttt tca ctc cac agt tac tct     1440
Ile Gln Arg Leu His Gly Leu Ser Ala Phe Ser Leu His Ser Tyr Ser
465                 470                 475                 480

cca ggt gaa att aat agg gtg gcc gca tgc ctc aga aaa ctt ggg gta     1488
Pro Gly Glu Ile Asn Arg Val Ala Ala Cys Leu Arg Lys Leu Gly Val
                485                 490                 495

ccg ccc ttg cga gct tgg aga cac cgg gcc cgg agc gtc cgc gct agg     1536
Pro Pro Leu Arg Ala Trp Arg His Arg Ala Arg Ser Val Arg Ala Arg
            500                 505                 510

ctt ctg gcc aga gga ggc agg gct gcc ata tgt ggc aag tac ctc ttc     1584
Leu Leu Ala Arg Gly Gly Arg Ala Ala Ile Cys Gly Lys Tyr Leu Phe
        515                 520                 525

aac tgg gca gta aga aca aag ctc aaa ctc act cca ata gcg gcc gct     1632
Asn Trp Ala Val Arg Thr Lys Leu Lys Leu Thr Pro Ile Ala Ala Ala
    530                 535                 540

ggc cag ctg gac ttg tcc ggc tgg ttc acg gct ggc tac agc ggg gga     1680
Gly Gln Leu Asp Leu Ser Gly Trp Phe Thr Ala Gly Tyr Ser Gly Gly
545                 550                 555                 560

gac att tat cac agc gtg tct cat gcc cgg ccc cgc tgg atc tgg ttt     1728
Asp Ile Tyr His Ser Val Ser His Ala Arg Pro Arg Trp Ile Trp Phe
                565                 570                 575
```

-continued

```
tgc cta ctc ctg ctt gct gca ggg gta ggc atc tac ctc ctc ccc aac      1776
Cys Leu Leu Leu Leu Ala Ala Gly Val Gly Ile Tyr Leu Leu Pro Asn
            580                 585                 590

cga tga ggatcc                                                       1788
Arg


<210> SEQ ID NO 2
<211> LENGTH: 593
<212> TYPE: PRT
<213> ORGANISM: Hepatitis C virus

<400> SEQUENCE: 2

Met Ala Ser Met Ser Tyr Ser Trp Thr Gly Ala Leu Val Thr Pro Cys
  1               5                  10                  15

Ala Ala Glu Glu Gln Lys Leu Pro Ile Asn Ala Leu Ser Asn Ser Leu
             20                  25                  30

Leu Arg His His Asn Leu Val Tyr Ser Thr Thr Ser Arg Ser Ala Cys
         35                  40                  45

Gln Arg Gln Lys Lys Val Thr Phe Asp Arg Leu Gln Val Leu Asp Ser
     50                  55                  60

His Tyr Gln Asp Val Leu Lys Glu Val Lys Ala Ala Ala Ser Lys Val
 65                  70                  75                  80

Lys Ala Asn Leu Leu Ser Val Glu Glu Ala Cys Ser Leu Thr Pro Pro
                 85                  90                  95

His Ser Ala Lys Ser Lys Phe Gly Tyr Gly Ala Lys Asp Val Arg Cys
            100                 105                 110

His Ala Arg Lys Ala Val Thr His Ile Asn Ser Val Trp Lys Asp Leu
        115                 120                 125

Leu Glu Asp Asn Val Thr Pro Ile Asp Thr Thr Ile Met Ala Lys Asn
    130                 135                 140

Glu Val Phe Cys Val Gln Pro Glu Lys Gly Gly Arg Lys Pro Ala Arg
145                 150                 155                 160

Leu Ile Val Phe Pro Asp Leu Gly Val Arg Val Cys Glu Lys Met Ala
                165                 170                 175

Leu Tyr Asp Val Val Thr Lys Leu Pro Leu Ala Val Met Gly Ser Ser
            180                 185                 190

Tyr Gly Phe Gln Tyr Ser Pro Gly Gln Arg Val Glu Phe Leu Val Gln
        195                 200                 205

Ala Trp Lys Ser Lys Lys Thr Pro Met Gly Phe Ser Tyr Asp Thr Arg
    210                 215                 220

Cys Phe Asp Ser Thr Val Thr Glu Ser Asp Ile Arg Thr Glu Glu Ala
225                 230                 235                 240

Ile Tyr Gln Cys Cys Asp Leu Asp Pro Gln Ala Arg Val Ala Ile Lys
                245                 250                 255

Ser Leu Thr Glu Arg Leu Tyr Val Gly Gly Pro Leu Thr Asn Ser Arg
            260                 265                 270

Gly Glu Asn Cys Gly Tyr Arg Arg Cys Arg Ala Ser Gly Val Leu Thr
        275                 280                 285

Thr Ser Cys Gly Asn Thr Leu Thr Cys Tyr Ile Lys Ala Arg Ala Ala
    290                 295                 300

Cys Arg Ala Ala Gly Leu Gln Asp Cys Thr Met Leu Val Cys Gly Asp
305                 310                 315                 320

Asp Leu Val Val Ile Cys Glu Ser Ala Gly Val Gln Glu Asp Ala Ala
                325                 330                 335
```

-continued

```
Ser Leu Arg Ala Phe Thr Glu Ala Met Thr Arg Tyr Ser Ala Pro Pro
            340                 345                 350

Gly Asp Pro Pro Gln Pro Glu Tyr Asp Leu Glu Leu Ile Thr Ser Cys
        355                 360                 365

Ser Ser Asn Val Ser Val Ala His Asp Gly Ala Gly Lys Arg Val Tyr
    370                 375                 380

Tyr Leu Thr Arg Asp Pro Thr Thr Pro Leu Ala Arg Ala Ala Trp Glu
385                 390                 395                 400

Thr Ala Arg His Thr Pro Val Asn Ser Trp Leu Gly Asn Ile Ile Met
                405                 410                 415

Phe Ala Pro Thr Leu Trp Ala Arg Met Ile Leu Met Thr His Phe Phe
            420                 425                 430

Ser Val Leu Ile Ala Arg Asp Gln Leu Glu Gln Ala Leu Asp Cys Glu
        435                 440                 445

Ile Tyr Gly Ala Cys Tyr Ser Ile Glu Pro Leu Asp Leu Pro Pro Ile
    450                 455                 460

Ile Gln Arg Leu His Gly Leu Ser Ala Phe Ser Leu His Ser Tyr Ser
465                 470                 475                 480

Pro Gly Glu Ile Asn Arg Val Ala Ala Cys Leu Arg Lys Leu Gly Val
                485                 490                 495

Pro Pro Leu Arg Ala Trp Arg His Arg Ala Arg Ser Val Arg Ala Arg
            500                 505                 510

Leu Leu Ala Arg Gly Gly Arg Ala Ala Ile Cys Gly Lys Tyr Leu Phe
        515                 520                 525

Asn Trp Ala Val Arg Thr Lys Leu Lys Leu Thr Pro Ile Ala Ala Ala
    530                 535                 540

Gly Gln Leu Asp Leu Ser Gly Trp Phe Thr Ala Gly Tyr Ser Gly Gly
545                 550                 555                 560

Asp Ile Tyr His Ser Val Ser His Ala Arg Pro Arg Trp Ile Trp Phe
                565                 570                 575

Cys Leu Leu Leu Leu Ala Ala Gly Val Gly Ile Tyr Leu Leu Pro Asn
            580                 585                 590

Arg


<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3

atagctagca tgtcttactc ttggagagg                                    29


<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4

ataggatcct catcggttgg ggaggagg                                     28


<210> SEQ ID NO 5
<211> LENGTH: 5
```

-continued

```
<212> TYPE: PRT
<213> ORGANISM: Hepatitis C virus

<400> SEQUENCE: 5

Ala Ser Met Ser Tyr
  1               5


<210> SEQ ID NO 6
<211> LENGTH: 6
<212> TYPE: PRT
<213> ORGANISM: Hepatitis C virus

<400> SEQUENCE: 6

Met Ala Ser Met Ser Tyr
  1               5


<210> SEQ ID NO 7
<211> LENGTH: 4
<212> TYPE: PRT
<213> ORGANISM: Hepatitis C virus

<400> SEQUENCE: 7

Ser Met Ser Tyr
  1


<210> SEQ ID NO 8
<211> LENGTH: 8
<212> TYPE: PRT
<213> ORGANISM: Hepatitis C virus

<400> SEQUENCE: 8

Ala Ser Met Ser Tyr Ser Trp Thr
  1               5


<210> SEQ ID NO 9
<211> LENGTH: 104
<212> TYPE: DNA
<213> ORGANISM: Artificial Sequence
<220> FEATURE:
<221> NAME/KEY: CDS
<222> LOCATION: (63)..(104)
<220> FEATURE:
<223> OTHER INFORMATION: Description of Artificial Sequence:vector
      sequence

<400> SEQUENCE: 9

ggagaccaca acggtttccc tctagaaata attttgttta actttaagaa ggagatatac     60

at atg gct agc atg act ggt gga cag caa atg ggt cgc gga tcc           104
   Met Ala Ser Met Thr Gly Gly Gln Gln Met Gly Arg Gly Ser
     1               5                  10


<210> SEQ ID NO 10
<211> LENGTH: 14
<212> TYPE: PRT
<213> ORGANISM: Artificial Sequence

<400> SEQUENCE: 10

Met Ala Ser Met Thr Gly Gly Gln Gln Met Gly Arg Gly Ser
  1               5                  10
```